United States Patent

Kruecke et al.

[11] Patent Number: 6,080,799
[45] Date of Patent: Jun. 27, 2000

[54] MIXTURES CONTAINING 1,1,1,3,3 PENTAFLUOROBUTANE

[75] Inventors: Werner Kruecke, Hannover; Lothar Zipfel, Laatzen, both of Germany

[73] Assignee: Solvay Fluor und Derivate GmbH, Hannover, Germany

[21] Appl. No.: 09/331,055

[22] PCT Filed: Dec. 11, 1997

[86] PCT No.: PCT/EP97/06908

§ 371 Date: Jun. 16, 1999

§ 102(e) Date: Jun. 16, 1999

[87] PCT Pub. No.: WO98/27145

PCT Pub. Date: Jun. 25, 1998

[30] Foreign Application Priority Data

Dec. 17, 1996 [DE] Germany .......................... 196 52 437
Jun. 16, 1997 [DE] Germany .......................... 197 25 360

[51] Int. Cl.$^7$ .................................................. C08J 9/14
[52] U.S. Cl. ........................... 521/131; 521/98; 521/155; 252/67; 252/69; 252/364; 510/177; 510/408; 510/412; 510/415
[58] Field of Search ............................ 521/98, 131, 155; 252/67, 69, 364; 510/177, 408, 412, 415

[56] References Cited

U.S. PATENT DOCUMENTS

| | | |
|---|---|---|
| 5,277,834 | 1/1994 | Bivens et al. ........................... 521/131 |
| 5,496,866 | 3/1996 | Sommerfeld . |
| 5,496,867 | 3/1996 | Sommerfeld . |
| 5,574,072 | 11/1996 | Werner et al. ........................... 521/131 |
| 5,624,970 | 4/1997 | Sommerfeld . |
| 5,646,196 | 7/1997 | Sommerfeld . |
| 5,730,894 | 3/1998 | Minor ....................................... 252/67 |
| 5,840,212 | 11/1998 | Doerge ..................................... 521/98 |
| 5,889,066 | 3/1999 | Doerge ..................................... 521/114 |

FOREIGN PATENT DOCUMENTS 298 419 A5  10/1983  Germany .
WO 96/12758  5/1996  WIPO .

*Primary Examiner*—John M. Cooney
*Attorney, Agent, or Firm*—Evenson, McKeown, Edwards & Lenahan, P.L.L.C.

[57] ABSTRACT

Mixtures containing 50 to 99% by weight of 1,1,1,3,3-pentafluorobutane and 1 to 50% by weight of at least one fluorohydrocarbon selected from 1,1,1,2-tetrafluoroethane, 1,1,1,3,3-pentafluoropropane, 1,1,1,3,3,3-hexafluoropropane, and 1,1,1,2,3,3,3-heptafluoropropane. The mixtures are extremely well suited for use as foaming gases for a blowing agent to produce foamed plastic materials, particularly polyurethane foams. The mixtures are not combustible and exhibit improved insulating properties, particularly when used at low temperatures.

15 Claims, No Drawings

MIXTURES CONTAINING 1,1,1,3,3 PENTAFLUOROBUTANE

BACKGROUND OF THE INVENTION

The present invention relates to mixtures with 1,1,1,3,3-pentafluorobutane (R 365 mfc) and their use for the manufacture of foamed plastics.

The use of partially fluorinated hydrocarbons as blowing agents for the manufacture of foamed plastics is already known. The international patent application WO 92/00345 discloses the use of partially fluorinated alkanes with 4 or 5 carbon atoms, which have a "tertiary structure", as blowing agents for the manufacture of polyurethane and polyisocyanurate foamed plastics.

The German Offenlegungsschrift DE 44 22 714 A1 discloses compositions, which contain 1,1,2-trifluoroethane, and the use of such compositions as blowing agents for the manufacture of foamed plastics. The international patent application WO 96/14354 discloses the manufacture of foamed plastics, for which a liquid blowing agent composition is used, which contains liquefied carbon dioxide under pressure. The blowing agent compositions may, moreover, contain fluorinated chlorinated hydrocarbons and fluorinated hydrocarbons, for example, also 1,1,1,3,3-pentafluorobutane (R 365 mfc). The German patent application 195 41 013 discloses, among other things, blowing agent compositions for the manufacture of highly resilient polyurethane foam. The blowing agent compositions comprise 50 to 95 parts by weight of 1,1,1,2-tetrafluoroethane and 5 to 50 parts by weight of 1,1-difluoroethane and/or readily volatile organic compounds. WO 96/12758 discloses blowing agent mixtures for the production of rigid polyurethane foams. The blowing agents may, if desired, contain fluorinated hydrocarbons such as 1,1,1,2-tetrafluoroethane, 1,1,1,3,3-pentafluoropropane, 1,1,1,3,3-pentafluorobutane, or 1,1,1,3,3,3-hexafluoropropane. The WO 96/30439 discloses azeotropic compositions comprising, among other things, 1,1,1,4,4,4-hexafluorobutane or perfluorohexane and certain $C_5$ or $C_6$ hydrocarbons. These compositions can be used as blowing agents for the manufacture of rigid polyurethane foams.

SUMMARY OF THE INVENTION

It is the object of the present invention to provide a method, which enables advantageous, foamed plastics, especially polyurethane foams, to be manufactured with simpler processing. It is furthermore an object of the present invention to indicate mixtures, which do not have a flash point and with which foamed polymer plastics, for example, with qualitatively advantageous properties, to be produced in a simple manner.

This object is achieved by the present invention.

Inventive mixtures, which can be used as blowing gas for the manufacture of foamed plastics, contain or consist of 50 to 99% by weight of 1,1,1,3,3-pentafluorobutane (HFC 365 mfc) and 1 to 50% by weight of at least one fluorinated hydrocarbon selected from the group consisting of 1,1,1,2-tetrafluoroethane, 1,1,1,3,3-pentafluoropropane, 1,1,1,3,3,3-hexafluoropropane and 1,1,1,2,3,3,3-heptafluoropropane.

1,1,1,3,3-pentafluorobutane lies at the limit of flammability. The inventive mixtures are distinguished owing to the fact that they do not represent flammable liquids at 20° C. They are suitable particularly for use as a blowing gas for the manufacture of foamed plastics; they can, however, also be used for other purposes such as a refrigerant, a solvent or a cleaning agent.

DESCRIPTION OF PREFERRED EMBODIMENTS

Preferred mixtures contain or consist of 80 to 99% by weight of 1,1,1,3,3-pentafluorobutane and 1 to 20% by weight of 1,1,1,2-tetrafluoroethane, 1,1,1,3,3,3-hexafluoropropane and/or 1,1,1,2,3,3,3-heptafluoropropane, especially mixtures which contain or consist of 80 to 99% by weight of 365 mfc and 1 to 20% by weight of 134a and/or 227 ea.

Especially preferred mixtures with 134a contain or consist of 91 to 95% by weight of 1,1,1,3,3-pentafluorobutane and 5 to 9% by weight of 1,1,1,2-tetrafluoroethane; mixtures, which consist of the given compounds in the given amounts have a boiling point of 20° C.

Especially preferred mixtures with 227 ea are those, which contain or consist of 80 to 99% by weight of 365 mfc and 1 to 20% by weight of 227 ea and especially of 85 to 89% by weight of 1,1,1,3,3-pentafluorobutane and 11 to 15% by weight of 1,1,1,2,3,3,3-heptafluoropropane; mixtures, which consist of the given compounds in the last-mentioned amounts, have a boiling point of about 23° C.

Mixtures with 245 fa, which contain 50% by weight of 1,1,1,3,3-pentafluorobutane and 50% by weight of 1,1,1,3,3-pentafluoropropane with a boiling point of the order of 22° C., are outstanding. In use, these mixtures have particularly good insulating properties.

Under standard conditions, the inventive mixtures are present in liquid form. The preferred mixtures are liquid at atmospheric pressure (about 1 atmosphere) and 20° C. They are advantageously used in this form if they are to be incorporated in plastics, or their pre-mixtures, which are to be foamed. They are particularly suitable as blowing agents for the manufacture of foamed plastics, for example, also by the extrusion method. For this method, the thermoplastic materials, which contain the blowing agent, are extruded directly into foamed panels, sheets or profiles. The plastic composition foams directly upon leaving the nozzle. For example, XPS and XPE foams (foams based on polystyrene or polyethylene) can be produced.

The inventive mixtures are particularly suitable for producing foams composed of isocyanates. They are also very suitable for the manufacture particularly of rigid foams and also of highly resilient foams composed of isocyanate. The manufacture of foams composed of isocyanate is known. Their manufacture and the basic materials, which can be used for this purpose, are disclosed, for example, in European patent application EP-A-0 381 986; in "Ullmanns Encyclopedia of Industrial Chemistry", 5$^{th}$ edition, Vol. A 21, pages 668–680; the international patent applications WO 92/00345, 96/30439, 96/14354 and the German Offenlegungsschrift DE 44 22 714 A1.

As starting materials, aliphatic, cycloaliphatic, araliphatic, aromatic and heterocyclic polyisocyanates, for example, with 2 to 4 isocyanate groups, can be used. They have an aliphatic hydrocarbon group with up to 18 carbon atoms, a cycloaliphatic hydrocarbon group with up to 15 carbon atoms, an aromatic hydrocarbon group with 6 to 15 carbon atoms or an araliphatic hydrocarbon group with 8 to 15 carbon atoms. Starting components, which are particularly preferred industrially are, for example, 2,4- and 2,6-toluylene diisocyanate, diphenyl methane diisocyanate, polymethylene polyphenyl isocyanate and their mixtures. So-called "modified" polyisocyanates can also be used, which contain carbodiimide groups, urethane groups, allophanate groups, isocyanurate groups, urea groups or biuret groups.

Further starting components are compounds with at least 2 hydrogen atoms, which can react with isocyanates. It is question here particularly of compounds with a molecular weight of 400 to 10,000, which preferably can have 2 to 8 hydroxyl groups and amino groups, thiol groups or carboxyl groups as well. Polyethers, polyesters, polycarbonates and polyester amides, which have 2 to 8 hydroxyl groups, are particularly suitable.

Optionally, compounds can also be used as starting components, which function as chain extension agents or as cross-linking agents and preferably have 2 to 8 hydrogen atoms capable of reacting with isocyanates. Usually, such agents have a molecular weight of 32 to 400. Instead of or in addition to hydroxyl groups, amino groups, thiol groups or carboxyl groups can also be present.

Optionally, further auxiliary materials and additives may be used. For example, chemical blowing agents, such as water, or other readily volatile organic substances, can be used, in addition, as physical blowing agents. Catalysts, such as tertiary amines, for example, dimethylhexylamine, and/or organometallic compounds, such as tin salts of carboxylic acids, can also be used. Further materials, which can be used, are surface-active additives, such as emulsifiers or foam stabilizers, such as siloxane polyether copolymers, reaction retarding agents, cell regulators, such as paraffins, fatty alcohols or polydimethylsiloxanes, pigments, dyes, flame retardants, such as phosphate esters or phosphonate esters, such as trischloroisopropyl phosphate. Furthermore, stabilizers against aging and weathering, plasticizers, fillers, dyes, antistats, nucleating agents, pore size regulators or materials with biocidal activity can be used.

Catalysts, which are very suitable, are described, for example, in the international patent application WO/96/14534. These include organic amines, aminoalcohols and aminoethers, such as morpholine compounds, for example, dimethylcyclohexylamine, diethanolamine, 2-dimethylaminoethyl 3-dimethylaminopropyl ether, 2-dimethylamino ether, 2,2-dimorpholinodiethyl ether, N,N-dimethylaminoethylmorpholine, N-dimethylmorpholine. Organometallic compounds, such as tin, cobalt or iron compounds, can also be used as catalyst. Tin dioctoate, cobalt naphthanate, dibutyl tin dilaurate and iron acetonyl acetate can be used, for example.

The invention additionally relates to blowing agents for the manufacture of foamed plastics, which are based on containing the inventive mixtures as blowing gas in an amount effective for the foaming. The blowing agents may consist of the inventive mixture. Aside from the inventive mixtures, the blowing agents may contain auxiliary materials and additives, such as water, one or more catalysts, flame retardants, emulsifiers, foam stabilizers, bonding agents, cross-linking agents, UV stabilizers, nucleating agents and optionally further blowing gases.

The invention further relates to plastic foams, obtained by using the inventive mixtures, especially those foams, which contain the inventive mixture in closed cells. Appropriate, inventive rigid polyurethane foams are preferred. They can be produced from foamable mixtures, which contain 1 to 50% by weight of the inventive mixtures as blowing gas, based on the polyol component.

Highly resilient polyurethane foams can also be produced using the inventive mixtures as blowing gases. They can be produced from mixtures of known raw materials, which contain 1 to 35% by weight of the inventive mixture as blowing gas, based on the polyol component set at 100% by weight.

The inventive mixtures have the advantage that they are incombustible liquids. On the other hand, pure 1,1,1,3,3-pentafluorobutane is at the threshold between substances that are and are not combustible. In addition, it has an excessively high boiling point for some applications. The inventive mixtures have the further advantage that, as blowing agents, they have advantages for the polyurethane foams and can be processed more easily. The given mixtures of R 365 mfc and R 134 a, in the ratio by weight of 93:7 and with a boiling point of about 20° C., as well as mixtures of R 365 mfc and R 227 ea, in the ratio of 87:13 and with an apparent boiling point of about 23° C., are particularly advantageous. The boiling of such mixtures corresponds to that of the previously used R 11. The fact that the inventive mixtures are not combustible denotes the status of a safety blowing agent for the application, as was previously ascribed to R 11. By adapting the effective boiling point of the blowing gases to the formulation, it was possible to improve the quality of the foams obtained with respect to the insulating behavior, especially when used for low temperatures. For example, the condensation at low temperatures is reduced or avoided. Correspondingly, the foams, especially the polyurethane foams, which were produced using an inventive blowing gas, are suitable particularly for insulating purposes in the construction and residence areas, especially also because the cell gases, contained in the closed cells, bring about high thermal insulation.

The following examples are intended to explain the invention in greater detail without, however, limiting its scope.

EXAMPLES

Example 1

Preparation of a Mixture of 1,1,1,3,3-Pentafluorobutane (R 365 mfc) and 1,1,1,2-Tetrafluoroethane (R 134a)
R 365 mfc (465 g) was transferred to a pressure vessel and 35 g of R 134a were added. A liquid mixture with a boiling point of about 20° C. resulted.

Example 2

Preparation of a Mixture of 1,1,1,3,3-Pentafluorobutane and 1,1,1,2,3,3,3-Heptafluoropropane (R 227 ea)
R 365 mfc (435 g) was transferred to a pressure vessel and 65 g of R 227 were added. A liquid mixture with a boiling point of about 23° C. resulted.

Example 3

Preparation of a Rigid Polyurethane Foam with R 365 mfc/R 134a as Blowing Gas
Formulation:
 1.) A mixture of
   100 g of polyol mixture of polyether polyols and an aromatic, brominated polyether polyol with a hydroxyl number of 450,
   20 g of trischloropropyl phosphate (as flame retardant)
   2 g of dimethylcyclohexylamine (as catalyst)
   1.5 g of siloxane polyether copolymer (as foam stabilizer)
   1 g of water
   29 g of the mixture produced in Example 1 (93 parts of 365 mfc and 7 parts of R 134a)
 2.) 131 g of 4,4'-diisocyanatodiphenylmethane
The materials, named under 1.), were mixed and the resulting mixture was mixed with the diisocyanate and foamed into a rigid polyurethane foam.
The foamed material had a density of 35 kg/m$^3$.

Example 4
Preparation of a Rigid Polyurethane Foam with R 365 mfc/R 227 ea as Blowing Agent Example 3 was repeated. The mixture (30 g), produced in Example 2, used as blowing gas.

The density of the foam obtained corresponded to that of the foam obtained in Example 3.

Example 5
Preparation of a Rigid Polyurethane Foam with R 365 mfc/R 134a as Blowing Agent, Glycerin Being Used as Polyol Formulation 1.) A mixture of
- 100 g of polyol component of a mixture of polyether polyols and an aromatic, brominated polyether polyol with a hydroxyl number of 450
- 11 g of dimethyl methyl phosphonate
- 1.8 g of a catalyst mixture
- 2 g of a siloxane polyether copolymer
- 1 g of water
- 32 g of the mixture of R 365 mfc/R134a produced in Example 1

2.) 170 g of 4,4'-diisocyanato diphenylmethane

The mixture, obtained by mixing the components named under 1., was foamed with the diisocyanate compound. The foaming resulted in a rigid polyurethane foam with an apparent density of 33 kg/m³.

Example 6
Rigid Polyurethane Foam with R 365 mfc/R 227 ea

Example 5 was repeated. However, this time 37 g of the mixture, prepared in Example 2 was used as physical blowing agent. The density of the foam was 30 g/liter.

Example 7
Preparation of a Highly Resilient Foam

Formulation:

1.) A mixture of
- 100 g of a polyether polyol with a hydroxyl number of 56
- 0.05 g of dibutyl tin dilaurate as catalyst
- 2 g of siloxane polyether copolymer
- 1 g of water
- 10 g of the R 365 mfc/R 134 a mixture prepared in Example 1

2.) 42 g of toluylene diisocyanate

The starting materials were mixed and foamed.

The resulting highly resilient polyurethane foam had an apparent density of 22 kg/m³.

Example 8
Preparation of a Resilient Polyurethane Foam

Example 7 was repeated. However, 12 g of the mixture of Example 2 were used.

The apparent density of the foam was 22 kg/m³.

What is claimed is:

1. A composition of matter comprising 50 to 99% by weight of 1,1,1,3,3-pentafluorobutane and 1 to 50% by weight of at least one fluorinated hydrocarbon selected from the group consisting of 1,1,1,2-tetrafluoroethane, 1,1,1,3,3-pentafluoropropane, 1,1,1,3,3,3-hexafluoropropane and 1,1,1,2,3,3,3-heptafluoropropane.

2. A composition of matter according to claim 1, consisting of 50 to 99% by weight of 1,1,1,3,3-pentafluorobutane and 1 to 50% by weight of at least one fluorinated hydrocarbon selected from the group consisting of 1,1,1,2-tetrafluoroethane, 1,1,1,3,3-pentafluoropropane, 1,1,1,3,3,3-hexafluoropropane and 1,1,1,2,3,3,3-heptafluoropropane.

3. A composition of matter according to claim 1, comprising 80 to 99% by weight of 1,1,1,3,3-pentafluorobutane and 1 to 20% by weight of at least one fluorinated hydrocarbon selected from the group consisting of 1,1,1,2-tetrafluoroethane, 1,1,1,3,3,3-hexafluoropropane and 1,1,1,2,3,3,3-heptafluoropropane.

4. A composition of matter according to claim 3, consisting of 80 to 99% by weight of 1,1,1,3,3-pentafluorobutane and 1 to 20% by weight of at least one fluorinated hydrocarbon selected from the group consisting of 1,1,1,2-tetrafluoroethane, 1,1,1,3,3,3-hexafluoropropane and 1,1,1,2,3,3,3-heptafluoropropane.

5. A composition of matter according to claim 1, comprising 91 to 95% by weight of 1,1,1,3,3-pentafluorobutane and 5 to 9% by weight of 1,1,1,2-tetrafluoroethane, said composition having a boiling point of about 20° C.

6. A composition of matter according to claim 5, consisting of 91 to 95% by weight of 1,1,1,3,3-pentafluorobutane and 5 to 9% by weight of 1,1,1,2-tetrafluoroethane.

7. A composition of matter according to claim 1, comprising 85 to 89% by weight of 1,1,1,3,3-pentafluorobutane and 11 to 15% by weight of 1,1,1,2,3,3,3-heptafluoropropane, said composition having a boiling point of about 23° C.

8. A composition of matter according to claim 7, consisting of 85 to 89% by weight of 1,1,1,3,3-pentafluorobutane and 11 to 15% by weight of 1,1,1,2,3,3,3-heptafluoropropane.

9. A composition of matter according to claim 1, consisting of 50% by weight of 1,1,1,3,3-pentafluorobutane and 50% by weight of 1,1,1,3,3-pentafluoropropane, said composition having a boiling point of 22° C.

10. A composition of matter according to claim 1, wherein said composition exists in liquid form under standard conditions.

11. A method of producing a foamed plastic material, said method comprising blowing said plastic material with a blowing agent comprising a composition of matter according to claim 1.

12. A method according to claim 11, wherein said foamed plastic material is a polyurethane foam material or an XPS/XPE foam material.

13. A method according to claim 11, wherein said foamed plastic material is a rigid polyurethane foam.

14. In a method of producing a foamed plastic material using a physical blowing agent composed of polyfluoroalkane blowing gases, the improvement comprising using as said blowing agent a composition of matter comprising 50 to 99% by weight of 1,1,1,3,3-pentafluorobutane and 1 to 50% by weight of at least one fluorinated hydrocarbon selected from the group consisting of 1,1,1,2-tetrafluoroethane, 1,1,1,3,3-pentafluoropropane, 1,1,1,3,3,3-hexafluoropropane and 1,1,1,2,3,3,3-heptafluoropropane.

15. A blowing agent for the production of foamed plastic material, said blowing agent comprising an effective plastic material foaming amount of a composition of matter comprising 50 to 99% by weight of 1,1,1,3,3-pentafluorobutane and 1 to 50% by weight of at least one fluorinated hydrocarbon selected from the group consisting of 1,1,1,2-tetrafluoroethane, 1,1,1,3,3-pentafluoropropane, 1,1,1,3,3,3-hexafluoropropane and 1,1,1,2,3,3,3-heptafluoropropane.

* * * * *